United States Patent
Maeda et al.

(10) Patent No.: US 11,505,812 B2
(45) Date of Patent: Nov. 22, 2022

(54) METHOD OF PRODUCING ERGOTHIONEINE

(71) Applicant: Mitsubishi Chemical Corporation, Chiyoda-ku (JP)

(72) Inventors: Takayuki Maeda, Tokyo (JP); Ryouichi Yamada, Tokyo (JP); Kohei Miyaoku, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 402 days.

(21) Appl. No.: 16/724,663

(22) Filed: Dec. 23, 2019

(65) Prior Publication Data

US 2020/0140904 A1 May 7, 2020

Related U.S. Application Data

(63) Continuation of application No. PCT/JP2018/024254, filed on Jun. 26, 2018.

(30) Foreign Application Priority Data

Jun. 27, 2017 (JP) .............................. JP2017-125469

(51) Int. Cl.
| | |
|---|---|
| C12P 17/10 | (2006.01) |
| C12P 13/04 | (2006.01) |
| C12P 7/18 | (2006.01) |
| C12N 1/14 | (2006.01) |
| C12N 1/20 | (2006.01) |
| A61K 31/4172 | (2006.01) |
| C12R 1/01 | (2006.01) |

(52) U.S. Cl.
CPC .......... *C12P 17/10* (2013.01); *A61K 31/4172* (2013.01); *C12N 1/14* (2013.01); *C12N 1/205* (2021.05); *C12P 7/18* (2013.01); *C12P 13/04* (2013.01); *C12R 2001/01* (2021.05)

(58) Field of Classification Search
None
See application file for complete search history.

(56) References Cited

U.S. PATENT DOCUMENTS

| 5,902,739 A | 5/1999 | Abe et al. |
| 2001/0008769 A1 | 7/2001 | Cho et al. |
| 2017/0321235 A1 | 11/2017 | Hara et al. |

FOREIGN PATENT DOCUMENTS

| JP | 10-215887 A | 8/1998 |
| WO | WO 98/44089 A1 | 10/1998 |
| WO | WO 2016/104437 A1 | 6/2016 |
| WO | WO 2016/121285 A1 | 8/2016 |

OTHER PUBLICATIONS

Japanese Office Action dated Sep. 28, 2021 in Japanese Patent Application No. 2019-526952 (with unedited computer generated English translation), 7 pages.
International Search Report dated Aug. 7, 2018 in PCT/JP2018/024254 filed on Jun. 26, 2018, 2 pages.
Melville, D, et al., "Ergothioneine in Microorganisms", Journal of Biological Chemistry, vol. 233, 1956, pp. 9-17.
Genghof, D., "Biosynthesis of Ergothioneine by Hercynine by Fungi and Actinomycetales", Journal of Bacteriology, vol. 103, No. 2, 1970, pp. 475-478.
Kasumi, T., "Monilella yeast and osmotic stress responses", Chemistries and Organisms, vol. 52, No. 7, 2014, 478-484 (with partial English Translation).
Japanese Office Action dated Jan. 5, 2022 in Japanese Patent Application No. 2019-526952 (with unedited computer generated English translation), 8 pages.

*Primary Examiner* — Michelle F. Paguio Frising
(74) *Attorney, Agent, or Firm* — Oblon, McClelland, Maier & Neustadt, L.L.P.

(57) ABSTRACT

An object of the present invention is to provide a simple method of producing ergothioneine. The present invention provides a method of producing ergothioneine comprising a step of culturing a microbe belonging to the genus *Moniliella* in a medium containing a carbon source to allow the microbe to produce ergothioneine.

8 Claims, No Drawings

METHOD OF PRODUCING ERGOTHIONEINE

TECHNICAL FIELD

The present invention relates to methods of producing ergothioneine. More particularly, the present invention relates to a method of producing ergothioneine using a microbe belonging to the genus *Moniliella*.

BACKGROUND ART

Ergothioneine is a kind of sulfur-containing amino acid known to have a high antioxidative effect and thus can remove a large amount of hydroxyl radical at high speed, whereby it is considered to be involved with reactive oxygen species removal in cells. Additionally, ergothioneine is deemed to demonstrate an elastase activity inhibitory action, a tyrosinase activity inhibitory action, an anti-inflammatory action, an anti-stress action, an anti-aging action, a wrinkle formation suppression action, and a lipid peroxide production suppression action.

Methods of producing ergothioneine include a chemosynthesis method, a method of extracting ergothioneine from a mycelium of mushrooms producing ergothioneine, and a method of extracting ergothioneine after culturing a microbe having an ergothioneine productivity.

The microbes having an ergothioneine productivity are disclosed in Non-Patent Literatures 1 and 2. According to these disclosures, many of the bacteria do not have the ergothioneine productivity, and there are some eucaryotes having the ergothioneine productivity, but examples disclosed in these literatures are extremely few in number.

Further, as a method of producing ergothioneine using a microbe having an ergothioneine productivity, a method is known for producing ergothioneine using microbes belonging to the genus *Methylobacterium*, which is a C1 compound-assimilating bacterium, microbes belonging to the genus *Rhodotorula*, which is a basidiomycetous yeast, or microbes belonging to the genus *Cryptococcus* (Patent Literature 1).

Furthermore, a method is also known for producing ergothioneine using a microbe belonging to the genus *Aspergillus*, which is a filamentous fungus of the *Ascomycota*. In this method, an ergothioneine productivity can be enhanced in comparison with a wild-type strain by overexpressing a gene encoding an ergothioneine synthesizing enzyme in the microbe (Patent Literature 2).

To the contrary, microbes belonging to the genus *Moniliella* of the *Basidiomycota* are known to produce erythritol (Patent Literature 3), but there is no report on a gene relating to ergothioneine synthesis or a synthesizing property of ergothioneine.

CITATION LIST

Patent Literature

Patent Literature 1: International Publication WO2016/104437

Patent Literature 2: International Publication WO2016/121285

Patent Literature 3: International Publication WO1998/044089

Non-Patent Literature

Non-Patent Literature 1: Dounald B. Melville et al, J. Biol. Chem. 1956, 223:9-17

Non-Patent Literature 2: Dorothy S. Genghof, J. Bacteriology, August 1970, P. 475-478

SUMMARY OF INVENTION

Technical Problem

An object of the present invention is to provide a simple method of producing ergothioneine.

Solution to Problem

The present inventors have conducted extensive studies to achieve the above object and performed metabolome analysis on an intracellular metabolite of microbes belonging to the genus *Moniliella*, and have found that microbes belonging to the genus *Moniliella* can produce ergothioneine, whereby the present invention was accomplished.

Specifically, the present invention is summarized as follows.

(1) A method of producing ergothioneine comprising a step of culturing a microbe belonging to the genus *Moniliella* in a medium containing a carbon source to allow the microbe to produce ergothioneine.

(2) The method according to (1), wherein the medium contains a carbon source in a concentration of 100 to 500 g/L.

(3) The method according to (1) or (2), wherein the microbe belonging to the genus *Moniliella* is at least one selected from the group consisting of *Moniliella pollinis*, *Moniliella megachiliensis*, *Moniliella acetoabutens*, *Moniliella suaveolens* var. *nigra*, and *Moniliella suaveolens* var. *suaveolens*.

(4) The method according to any of (1) to (3), wherein the microbe belonging to the genus *Moniliella* is at least one selected from the group consisting of *Moniliella pollinis* CBS461.67, *Moniliella megachiliensis* CBS567.85, *Moniliella suaveolens* var. *nigra* CBS223.32, *Moniliella suaveolens* var. *nigra* CBS382.36, *Moniliella suaveolens* var. *nigra* CBS223.79, *Moniliella acetoabutens* CBS170.66, *Moniliella acetoabutens* CBS171.66, *Moniliella acetoabutens* CBS594.68, *Moniliella suaveolens* var. *suaveolens* CBS101.20, and *Moniliella suaveolens* var. *suaveolens* CBS127.42.

(5) The method according to any of (1) to (4), wherein the microbe belonging to the genus *Moniliella* is at least one selected from the group consisting of *Moniliella pollinis* MCI3554 (accession number FERM BP-6170), *Moniliella pollinis* MCI3555 (accession number FERM BP-6171), *Moniliella pollinis* MCI3371 (accession number FERM BP-6173), and *Moniliella megachiliensis* MCI3369 (accession number FERM BP-6172), or a mutant thereof.

(6) The method according to any of (1) to (5), wherein the step further comprises allowing the microbe to produce at least one selected from the group consisting of sugar alcohols, alcohols, and organic acids.

(7) The method according to any of (1) to (6), further comprising collecting ergothioneine from the culture obtained in the above step.

(8) The method according to any of (1) to (7), further comprising collecting at least one selected from the group consisting of sugar alcohols, alcohols, and organic acids from the culture obtained in the above step.

(9) The method according to any of (6) to (8), wherein the sugar alcohol is erythritol.

(10) A method of producing erythritol, comprising: a step of culturing a microbe belonging to the genus *Moniliella* in a medium containing a carbon source to allow the microbe to produce erythritol and ergothioneine.

According to the method of producing ergothioneine of the present invention, ergothioneine can be intracellularly accumulated in a short period of time and thus ergothioneine can be produced simply and in a short period of time.

Hereinafter, the present invention is specifically described but is not limited to the following embodiments and can be carried out in various modifications as long as it stays within the scope of the gist of the present invention. Further, the present specification encompasses the contents described in the specification and drawings of a Japanese patent application (Japanese Patent Application No. 2017-125469) filed on Jun. 27, 2017, which is the basis of claiming priority of the present application.

The present invention is a method of producing ergothioneine comprising a step of culturing a microbe belonging to the genus *Moniliella* using a medium containing a carbon source to allow the microbe to produce ergothioneine (hereinafter, "Step (1)"), and preferably a method of producing ergothioneine further comprising, after the above Step (1), a step of collecting ergothioneine from the culture obtained in the above Step (1) (hereinafter, "Step (2)").

Hereinafter, the above Steps (1) and (2) are sequentially described.

[Step (1)]

Step (1) is a step of culturing a microbe belonging to the genus *Moniliella* in a medium containing a carbon source to allow the microbe to produce ergothioneine.

In the present invention, the microbe belonging to the genus *Moniliella* is not particularly limited as long as microbes are classified into the division *Basidiomycota*, subdivision Agaricomycotina, class Tremellomycetes, and genus *Moniliella*. The microbe belonging to the genus *Moniliella* that is used in the present invention is preferably at least one selected from the group consisting of *Moniliella pollinis*, *Moniliella megachiliensis*, *Moniliella acetoabutens*, *Moniliella suaveolens* var. *nigra*, and *Moniliella suaveolens* var. *suaveolens*. Of these, *Moniliella pollinis* is more preferable in the aspect of being used for the industrial production of erythritol.

Further, the microbe belonging to the genus *Moniliella* is preferably at least one selected from the group consisting of *Moniliella pollinis* CBS461.67, *Moniliella megachiliensis* CB S567.85, *Moniliella suaveolens* var. *nigra* CBS223.32, *Moniliella suaveolens* var. *nigra* CB S382.36, *Moniliella suaveolens* var. *nigra* CB S223.79, *Moniliella acetoabutens* CB S170.66, *Moniliella acetoabutens* CBS171.66, *Moniliella acetoabutens* CBS594.68, *Moniliella suaveolens* var. *suaveolens* CB S101.20, and *Moniliella suaveolens* var. *suaveolens* CBS127.42, all of which are registered in the CBS-KNAW culture collection in the Netherlands.

Of the above, the microbe belonging to the genus *Moniliella* is more preferably at least one deposited strain selected from the group consisting of *Moniliella pollinis* MCI3554 (accession number FERM BP-6170), *Moniliella pollinis* MCI3555 (accession number FERM BP-6171), *Moniliella pollinis* MCI3371 (accession number FERM BP-6173), and *Moniliella megachiliensis* MCI3369 (accession number FERM BP-6172). Further, the microbe belonging to the genus *Moniliella* may be a mutant of the above deposited strains. A mutant of strain can be created using a common mutagenesis method. Examples of such a mutagenesis method include UV or X-ray irradiation for introducing a mutation by physically damaging DNA, and a treatment using an alkylating reagent such as N-methyl-N'-nitro-N-nitrosoguanidine (NTG) or ethyl methanesulfonate (EMS) for introducing a mutation by chemically damaging DNA.

Furthermore, the microbe belonging to the genus *Moniliella* can also be obtained from the nature. For example, microbes belonging to the genus *Moniliella* are widely distributed in the natural soil and tend to grow in the environment having a high sugar concentration. For this reason, such a microbe can be obtained from soils, high sugar concentration substances such as tree saps and dropped fruits, food products such as jams, marmalades and honeys, and the body surface of bee larva. Additionally, these microbes are known to be attached to farm crops such as vegetables and fruits and pollute drinks and foods made from these farm crops, and thus can be obtained from the environments for producing drinks and foods. Further, these microbes have higher acetic acid resistance than other bacteria and thus acidophilous *Moniliella acetoabutans* can be obtained from vinegars and pickles, and *Moniliella suaveolens* can also be obtained from food products containing an oil.

Whether or not a microbe belonging to the genus *Moniliella* produces ergothioneine can be evaluated using a common method. For example, the obtained microbe is proliferated, then cells are separated, an extraction operation of ergothioneine from the separated cells is carried out, and an evaluation can be made whether ergothioneine is detected or measured from the obtained extract using a known quantitative method such as high-performance liquid chromatography or gas chromatography.

In light of the fact that *Moniliella pollinis* and *Moniliella megachiliensis* have an ergothioneine productivity, which is demonstrated in Examples to be described later, it is understandable that microbes belonging to the genus *Moniliella*, which are linearly closely related to *Moniliella pollinis* and *Moniliella megachiliensis*, have the ergothioneine productivity. Similarly, it is understandable that microbes belonging to the genus *Moniliella* having genes related to ergothioneine synthesis such as an ergothioneine 1 (Egt-1) gene are capable of producing ergothioneine.

Microbes belonging to the genus *Moniliella* described above or strains thereof can be used alone or in combination. Additionally, when a microbe having a high erythritol productivity is selected in Step (1), erythritol can also be produced in addition to ergothioneine.

In Step (1), a microbe belonging to the genus *Moniliella* is cultured using a medium containing a carbon source.

For the medium, it is preferable to use a liquid medium in which a carbon source, a nitrogen source, optionally, an inorganic salt and/or a growth factor are dissolved in water.

For the carbon source contained in a medium, fermentable sugars such as glucose, fructose, and glycerol are used. Of these, because of its easy availability at a low cost, glucose or fructose is preferable, and glucose is particularly preferable. These carbon sources can be used alone or in combination.

When glucose is used as a carbon source, a concentration of the carbon source contained in a medium is typically 100 g/L or more, preferably 200 g/L or more, and more preferably 250 g/L or more, and typically 500 g/L or less, and preferably 450 g/L or less. Further, examples of the concentration range of the carbon source include 100 to 500 g/L, 100 to 450 g/L, 100 to 300 g/L, 200 to 500 g/L, 200 to 450 g/L, 200 to 300 g/L, 250 to 500 g/L, 250 to 450 g/L, and 250 to 300 g/L, but not limited thereto. As described above, when a concentration of the carbon source is comparatively high, an effect of preventing (reducing) the contamination during culture is obtained.

A carbon source may also be dividedly added during culture. Ergothioneine is produced from a carbon source by the microbe used in the present invention.

For the nitrogen source contained in a medium, various organic and inorganic nitrogen compounds such as ammonium salts, urea, peptones, microbe extracts (for example, yeast extracts), and corn steep liquors are used. For the inorganic salts, metal salts such as various phosphates, sulfates, magnesium, potassium, manganese, iron, and zinc are used. Additionally, factors promoting the growth of microbes such as vitamins, nucleotides, and amino acids can be added as necessary as a growth factor. Further, it is preferable to add a suitable amount of a commercial defoamer to reduce foams caused by medium components during culture.

In the present invention, the culture conditions for the microbe belonging to the genus *Moniliella* are preferably set as follows.

The culture temperature is not particularly limited but typically 25° C. or more, and preferably 27° C. or more, and typically 37° C. or less, and preferably 35° C. or less.

The culture time is not particularly limited but the culture is preferably carried out until a carbon source is consumed. Specifically, the culture can be carried out for 24 hours to 8 days. In the production method of the present invention, the microbe is allowed to produce ergothioneine in a shorter period of time (e.g., 24 hours to 3 days) than the conventional one.

The culture is carried out preferably under aerobic conditions such as aeration, stirring, or shaking.

The above culture conditions are expected to vary depending on a microbe used but preferable conditions can be found by carrying out preliminary experiments by changing conditions stepwise for a microbe used.

An amount of intracellular ergothioneine thus produced can be measured by a typically used method which has been already known such as high speed liquid chromatography or gas chromatography, and more specifically a method described in the Examples.

In the present invention, Step (1) can comprise a step of further allowing the microbe belonging to the genus *Moniliella* to produce at least one selected from the group consisting of sugar alcohols, alcohols, and organic acids.

In the present invention, the sugar alcohol is not limited and examples include erythritol, xylitol, sorbitol, mannitol, and lactitol, preferably erythritol. Examples of the alcohol include methanol, ethanol, 1-propanol, 2-propanol, 1-butanol, 2-butanol, 1,3-propanediol, 1,2-propanediol, 1,4-butanediol, 1,3-butanediol, and 2,3-butanediol. Examples of the organic acid include acetic acid, propionic acid, butyric acid, pyruvic acid, lactic acid, malic acid, fumaric acid, succinic acid, 2-oxoglutaric acid, citric acid, isocitric acid, alanine, valine, serine, glutamic acid, and lysine, but not limited thereto.

[Step (2)]

Step (2) is a step of collecting (for example, separation, cell disruption, heat treatment, extraction, and purification) ergothioneine from the culture obtained in the above Step (1).

The method of collecting ergothioneine from the culture obtained in the above Step (1) is not particularly limited.

When ergothioneine is collected from the culture obtained in Step (1), ergothioneine may be directly extracted from the culture. It is preferable to collect cells from the culture by an operation such as filtration or centrifugation, and extract ergothioneine from the collected cells. In this case, cells may be used directly, or cells dried after collected and cells further crushed may also be used.

Further, when a microbe having a high sugar alcohol (for example, erythritol) productivity is selected in Step (1) and the microbe is allowed to also produce a sugar alcohol in addition to ergothioneine, the culture obtained in Step (1) can be separated into cell fractions and other solution fractions to collect (e.g., extract) ergothioneine from the cell fractions and collect a sugar alcohol from other solution fractions. In this way, an otherwise discarded cell fraction can be effectively utilized.

The solvent used for extraction is not particularly limited as long as ergothioneine is dissolved and examples include organic solvents such as methanol, ethanol, isopropanol, and acetone; water-containing organic solvents in which these organic solvents and water are mixed; and water, warm water, and hot water. The temperature of a solvent is typically 60 to 98° C., and preferably 80 to 98° C.

Ergothioneine is extracted, preferably, optionally while disrupting cells, after a solvent is added.

The extract obtained by the above extraction may be purified as necessary. The purification method is not particularly limited and examples include centrifugation, filter filtration, ultrafiltration, gel filtration, separation by solubility difference, solvent extraction, chromatography (adsorption chromatography, hydrophobic chromatography, cation exchange chromatography, anion exchange chromatography, reversed phase chromatography, etc.), crystallization, activated carbon treatment, and membrane treatment.

EXAMPLES

Hereinafter, the present invention is described in further detail with reference to Examples but is not limited by the following Examples unless it goes beyond the gist thereof.

1. Production of Ergothioneine by Microbes Belonging to the Genus *Moniliella*

Examples 1 to 3

Microbes belonging to the genus *Moniliella* were investigated for the production of ergothioneine.

(1) Strain

For the microbes belonging to the genus *Moniliella*, Example 1 used *Moniliella pollinis* (hereinafter, sometimes referred to as "*M. Pollinis*") MCI3554 (accession number FERM BP-6170), Example 2 used *M. Pollinis* MCI3555 (accession number FERM BP-6171), and Example 3 used *M. Pollinis* MCI3371 (accession number FERM BP-6173). *M. pollinis* MCI3555 is a mutant strain of a wild-type strain *M. pollinis* MCI3554, and *M. pollinis* MCI3371 is a mutant strain of *M. pollinis* CBS461.67.

(2) Culture and Cell Collection of Each Strain

A 100 g/L solution of a yeast extract (MEAST P1G manufactured by ASAHI FOOD & HEALTHCARE, CO., LTD) and a 333 g/L solution of glucose (anhydrous crystalline dextrose #300 manufactured by NIHON SHOKUHIN KAKO CO., LTD.) were separately sterilized at 120° C. for 20 minutes, subsequently each strain was inoculated to a mixture of 5 ml and 45 ml of each solution in similarly sterilized 500 ml conical flasks with baffles, and cultured at 30° C. at 180 rpm for 3 days. Upon completion of the culture, 5 ml each of the culture solutions was dispensed and centrifuged at 4° C. at 8000×g for 5 minutes. The obtained cells were suspended in 0.9 wt % saline, centrifuged at 4° C. at 8000×g for 5 minutes, suspended again in saline and centrifuged to collect cells. The collected cells were measured for the weight on a wet cell weight basis. Additionally, one tube of the obtained wet cell samples was lyophilized overnight to measure a dry cell weight.

Measurement results of the obtained wet cell weights, dry cell weight, and water contents are shown in Table 1.

TABLE 1

|  | Strain | Wet cell weight (g) | Dry cell weight (g) | Water content |
|---|---|---|---|---|
| Example 1 | MCI 3554 | 0.799 | 0.264 | 33.0% |
| Example 2 | MCI 3371 | 0.453 | 0.124 | 27.4% |
| Example 3 | MCI 3555 | 0.736 | 0.225 | 30.5% |

(3) Investigation of Ergothioneine Production

The wet cells obtained by the collection described above were suspended in water having a weight two times the wet cell weight, and then treated at 95° C. for 20 minutes to extract ergothioneine in the cells. Subsequently, centrifugation was carried out at room temperature at 10000×g for 5 minutes, 1 ml of the supernatant was collected and lyophilized overnight. The dried solid substance obtained by lyophilization was dissolved again in 500 µl of water, subsequently centrifuged at room temperature at 10000×g for 5 minutes, and the supernatant was filtered using a 0.2 µm filter to measure a concentration of ergothioneine in the filtrate.

In the present Example, an amount of ergothioneine was determined by HPLC using HILICpak VG-50 4E (SHOWA DENKO K.K., 4.6×250 mm). Ergothioneine was eluted using acetonitrile/5 mM ammonium acetate aqueous solution=70/30 as an eluent at a flow rate of 0.6 ml/min and measured with an absorbance at a wavelength of 260 nm. Under the present measurement conditions, the elution of ergothioneine was confirmed after 7.99 min.

Table 2 shows the amount of ergothioneine production by the dry cell weight for each strain of Examples 1 to 3. As a result of culture for 3 days in the medium described above, all the strains were confirmed to have produced ergothioneine.

TABLE 2

|  | Strain | Amount of ergothioneine production (µg/gDCW/h) |
|---|---|---|
| Example 1 | MCI 3554 | 12.1 |
| Example 2 | MCI 3371 | 4.1 |
| Example 3 | MCI 3555 | 4.2 |

Examples 4 to 8

Production test of ergothioneine under conditions with different glucose concentrations

*M. Pollinis* MCI3554 was compared in the ergothioneine productivity under the conditions based on Example 1 in which initial glucose concentrations during the flask culture were changed in the range of 100 to 500 g/L.

*M. Pollinis* MCI3554 was cultured under the same conditions as in Example 1 except the initial glucose concentration, and the results of ergothioneine production are shown in Table 3. In the present Example, the ergothioneine production was maximized when an initial glucose concentration was 300 g/L.

TABLE 3

|  | Glucose (g/L) | Wet cell weight (g) | Dry cell weight (g) | Water content | Amount of ergothioneine production (µg/gDCW/h) |
|---|---|---|---|---|---|
| Example 4 | 100 | 0.460 | 0.129 | 28.2% | 9.2 |
| Example 5 | 200 | 0.683 | 0.211 | 30.9% | 9.5 |
| Example 6 | 300 | 0.799 | 0.264 | 33.0% | 12.1 |
| Example 7 | 400 | 0.774 | 0.266 | 34.3% | 8.0 |
| Example 8 | 500 | 0.693 | 0.239 | 34.4% | 1.4 |

Example 9

(1) Strain

In Example 9, *Moniliella megachiliensis* (hereinafter, sometimes referred to as "*M. Megachiliensis*") MCI3369 (accession number FERM BP-6172) was used as the microbe belonging to the genus *Moniliella*. *M. megachiliensis* MCI3369 is a mutant strain of *M. megachiliensis* CBS567.85.

(2) Production Test of Ergothioneine Under Conditions with Different Glucose Concentrations

*M. megachiliensis* MCI3369 was compared in the ergothioneine productivity under the conditions in which initial glucose concentrations during the flask culture were changed in the range of 100 to 500 g/L as in the conditions in Examples 4 to 8. *M. megachiliensis* MCI3369 was cultured and ergothioneine production was investigated. As a result, it was confirmed that ergothioneine was produced at all concentrations.

The above Examples 1 to 9 verified that when a microbe belonging to the genus *Moniliella* is cultured in a medium containing a carbon source and allowed to produce ergothioneine, ergothioneine can be produced simply and in a short period of time.

2. Investigation of Erythritol Production

The supernatant collected after centrifuging the culture solution of each strain in the above item "1" was collected to measure a concentration of erythritol.

An amount of erythritol was determined by HPLC using MCI GEL™ CK08EH (Mitsubishi Chemical Corporation, 8×300 mm). Erythritol was eluted using a 1.175 g/L phosphoric acid aqueous solution as an eluent at a flow rate of 0.6 ml/min at a column temperature of 50° C. and measured by detection using a refractive index detector (RI). Under the present measurement conditions, the elution of erythritol was confirmed after 13.02 min.

Table 4 shows the amount of erythritol production in the culture solution of each strain. As shown in Table 4, all the strains measured were confirmed to have produced erythritol.

TABLE 4

| 3-Day (72-h) culture | | |
|---|---|---|
|  | Strain | Amount of erythritol accumulated (g/L) |
| Example 1 | MCI 3554 | 58.3 |
| Example 2 | MCI 3371 | 4.7 |
| Example 3 | MCI 3555 | 44.2 |

TABLE 4-continued

3-Day (72-h) culture

| Strain | | Amount of erythritol accumulated (g/L) |
|---|---|---|
| Example 4 | MCI 3554 | 23.2 |
| Example 5 | MCI 3554 | 68.8 |
| Example 6 | MCI 3554 | 58.3 |
| Example 7 | MCI 3554 | 50.0 |
| Example 8 | MCI 3554 | 28.1 |

The above results revealed that, in the method of the present invention, when a microbe belonging to the genus *Moniliella* is cultured in a medium containing a carbon source, the microbe can be allowed to not only produce ergothioneine but also to produce a sugar alcohol. Additionally, it was verified that when a sugar alcohol is collected from the culture supernatant of the ergothioneine producing strain, a sugar alcohol in addition to ergothioneine can be produced.

These results further revealed that, in the method of the present invention, ergothioneine can be obtained from cells and organic compounds such as sugar alcohols, alcohols, and organic acids can be obtained from the culture supernatant in a single culture solution.

As evident in the above results, according to the method of the present invention, ergothioneine and a sugar alcohol can be obtained from a single (same) culture solution. Therefore, the method of the present invention is extremely economic- and time-efficient and hence an industrially useful method. Further, according to the method of the present invention, ergothioneine can be obtained from cells which have been otherwise discarded. Therefore, the method of the present invention is an extremely useful method capable of reducing the burden on environment by effectively utilizing wastes.

*Moniliella pollinis* MCI 3554 and *Moniliella pollinis* MCI 3555 described in the present specification were deposited internationally under accession numbers FERM BP-6170 and FERM BP-6171, respectively, as of Nov. 19, 1997 in the International Patent Organism Depositary, National Institute of Technology and Evaluation (NITE-IPOD) (former Life Engineering Research Institute of the Agency of Industrial Science and Technology, Ministry of International Trade and Industry) located at #122, 2-5-8 Kazusakamatari, Kisarazu-shi, Chiba (zip code: 292-0818). *Moniliella pollinis* MCI 3371 was transferred to the international depositary under accession number FERM BP-6173 as of Nov. 19, 1997 in the same Center. *Moniliella megachiliensis* MCI 3369 was transferred to the international depositary under accession number FERM BP-6172 as of Nov. 19, 1997 in the same depositary.

The invention claimed is:

1. A method of producing ergothioneine, comprising: culturing a microbe belonging to the genus *Moniliella* in a medium containing a carbon source to allow the microbe to produce ergothioneine; and collecting ergothioneine from cell fractions obtained in the culturing.

2. The method according to claim 1, wherein the medium contains a carbon source in a concentration of 100 to 500 g/L.

3. The method according to claim 1, wherein the microbe belonging to the genus: *Moniliella* is at least one selected from the group consisting of *Moniliella pollinis, Moniliella megachiliensis, Moniliella acetoabutens, Moniliella suaveolens* var. *nigra*, and *Moniliella suaveolens* var. *suaveolens*.

4. The method according to claim 1, wherein the microbe belonging to the genus *Moniliella* at least one selected from the group consisting of *Moniliella pollinis* MCI3554 (accession number FERM BP-6170), *Moniliella pollinis* MCI3555 (accession number FERM BP-6171), *Moniliella pollinis* MCI3371 (accession number FERM BP-6173), and *Moniliella megachiliensis* MCI3369 (accession number FERM BP-6172), or a mutant thereof.

5. The method according to claim 1, wherein the step further comprises allowing the microbe to produce at least one selected from the group consisting of sugar alcohols, alcohols, and organic acids.

6. The method according to claim 5, wherein the sugar alcohol is erythritol.

7. The method according to claim 1, further comprising collecting at least one selected from the group consisting of sugar alcohols, alcohols, and organic acids from the culture obtained in the step.

8. The method according to claim 7, wherein the sugar alcohol is erythritol.

* * * * *